(12) United States Patent
Sekiguchi et al.

(10) Patent No.: US 11,118,173 B2
(45) Date of Patent: Sep. 14, 2021

(54) METHOD OF COLLECTING A NUCLEIC ACID(S)

(71) Applicant: Toray Industries, Inc., Tokyo (JP)

(72) Inventors: Shota Sekiguchi, Kamakura (JP); Shinjiro Sawada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/556,954

(22) PCT Filed: Mar. 18, 2016

(86) PCT No.: PCT/JP2016/058658
§ 371 (c)(1),
(2) Date: Sep. 8, 2017

(87) PCT Pub. No.: WO2016/152763
PCT Pub. Date: Sep. 29, 2016

(65) Prior Publication Data
US 2018/0051274 A1    Feb. 22, 2018

(30) Foreign Application Priority Data

Mar. 20, 2015  (JP) .............................. JP2015-057760

(51) Int. Cl.
| | | |
|---|---|---|
| *C12N 15/10* | (2006.01) | |
| *C12N 15/09* | (2006.01) | |
| *C12M 1/00* | (2006.01) | |
| *B01J 21/04* | (2006.01) | |
| *B01J 23/00* | (2006.01) | |
| *G01N 33/48* | (2006.01) | |

(52) U.S. Cl.
CPC .......... *C12N 15/1006* (2013.01); *B01J 21/04* (2013.01); *B01J 23/002* (2013.01); *C12M 1/00* (2013.01); *C12N 15/09* (2013.01); *G01N 33/48* (2013.01)

(58) Field of Classification Search
CPC .. C12N 15/1006; C12N 15/1003; C07H 1/00; H05K 1/0259; H05K 1/0393; H05K 1/167; H05K 2201/09063; H05K 2201/09781; H05K 2203/1545; H05K 3/0097; C12Q 1/6806; C12Q 2523/308; B01J 21/04
See application file for complete search history.

(56) References Cited

U.S. PATENT DOCUMENTS

| | | | |
|---|---|---|---|
| 5,234,809 A | 8/1993 | Boom et al. | |
| 6,383,393 B1 | 5/2002 | Colpan et al. | |
| 2002/0132242 A1 | 9/2002 | Gerdes et al. | |
| 2003/0162853 A1* | 8/2003 | Smiley ................. | B01D 15/325 521/64 |
| 2005/0208510 A1* | 9/2005 | Latham ............... | C12N 15/1013 435/6.12 |
| 2006/0166241 A1* | 7/2006 | Shim ................... | C12N 15/1006 435/6.12 |
| 2007/0015165 A1 | 1/2007 | Chen et al. | |
| 2008/0187979 A1* | 8/2008 | Mori ................... | C12N 15/1003 435/195 |
| 2009/0186357 A1* | 7/2009 | Mauk .................... | B01L 3/5027 435/6.15 |
| 2011/0130558 A1 | 6/2011 | Ritt et al. | |
| 2011/0319506 A1 | 12/2011 | Erbacher et al. | |

FOREIGN PATENT DOCUMENTS

| | | |
|---|---|---|
| JP | 11-155567 A | 6/1999 |
| JP | 2003-235555 | 8/2003 |
| JP | 2003-235555 | 8/2003 |
| JP | 2005-505269 A | 2/2005 |
| JP | 2007-529229 | 10/2007 |
| JP | 2007-529229 A | 10/2007 |
| JP | 2011-522529 A | 8/2011 |
| JP | 2013-505719 A | 2/2013 |
| WO | 92/18514 A1 | 10/1992 |
| WO | 2005-089929 | 9/2005 |

OTHER PUBLICATIONS

Extended European Search Report dated Sep. 24, 2018, of counterpart European Application No. 16768666.6.
Office Action dated Sep. 10, 2019, of counterpart European Application No. 16768666.6.
First Office Action dated Mar. 2, 2020, of counterpart Chinese Application No. 201680015280.0 with an English translation.

\* cited by examiner

*Primary Examiner* — Betty J Forman
(74) *Attorney, Agent, or Firm* — DLA Piper LLP (US)

(57) ABSTRACT

A method of collecting a nucleic acid(s) from a biological sample includes step a) mixing an aluminum oxide support with a water-soluble neutral polymer adsorbed on a surface thereof and a solution containing a nucleic acid(s), thereby adsorbing the nucleic acid(s) to the support; step b) separating the support on which the nucleic acid(s) is/are adsorbed from the solution mixed in step a); and step c) collecting the nucleic acid(s) by adding an eluent to the support on which the nucleic acid(s) is/are adsorbed and which is separated in step b).

8 Claims, No Drawings

METHOD OF COLLECTING A NUCLEIC ACID(S)

TECHNICAL FIELD

This disclosure relates to a method of collecting a nucleic acid(s), an aluminum oxide support with a water-soluble neutral polymer adsorbed on the surface thereof, and a kit for collecting a nucleic acid(s).

BACKGROUND

The development of experimental techniques using nucleic acids has allowed for search of new genes and analysis of the genes. The human genome has been analyzed to identify a disease such as cancer, and the genome of pathogens has been analyzed to identify the infection of the pathogens. Thus, screening tests and clinical tests using gene analysis have been performed in the medical field as well.

For the target in gene analysis, not only long-chain nucleic acids such as a genome, but also short-chain nucleic acids have attracted attention. miRNAs which were discovered in recent years are single-chain RNAs of not less than 18 bases and not more than 25 bases, and are biosynthesized from pre-miRNAs of not less than 60 bases and not more than 90. miRNAs are believed to be related to diseases because they have a function to control protein synthesis and gene expression, and thus have attracted attention as a target of gene analysis. A method such as a metagenomic diagnosis method, in which nucleic acid fragments of several hundreds of base pairs derived from pathogens in a clinical sample are analyzed comprehensively by a next-generation sequencer has also attracted attention as a new gene analysis method. It is recognized that the target of the current gene analysis has diversified as the gene search has developed. Therefore, for the method of collecting nucleic acids as well, in response to the target diversification in gene analysis, a method of collecting nucleic acids ranging from those of several dozen bases such as miRNAs to long-chain nucleic acids such as genomes has been demanded.

What is first required in performing gene analysis is a step of collecting nucleic acids from a biological sample. If the nucleic acids can be collected with a high purity and high yield, a highly sensitive gene detection can be attained in the detection reaction afterwards. Representative examples of methods of collecting nucleic acids include phenol-chloroform extraction, ethanol precipitation and nucleic acid adsorption on silica.

In particular, the most common method is the Boom method, disclosed in U.S. Pat. No. 5,234,809 Specification, in which nucleic acids are adsorbed on a metal oxide containing silica, then eluted, and then collected. This method is characterized by the concentration of the nucleic acids along with the collection of the nucleic acids from the nucleic acid-adsorbed silica by a centrifugation. However, the Boom method requires the use of organic solvents such as alcohol in the adsorption step of the nucleic acids, which causes a problem of a more complicated collection procedure, disposal of the solvents or the like. In addition, there is also a problem in which the isolated nucleic acids are contaminated with these organic solvents, and the later detection reaction is affected.

Japanese National-Phase Publication No. 2011-522529 discloses that a nucleic acid having the length of not less than 300 base pairs and not more than 1000 base pairs exhibits inferior adsorption property on silica compared to the adsorption property of a longer nucleic acid. Thus, it is assumed that the collection of even shorter pre-miRNAs or miRNAs is difficult. Since gene analysis is also utilized in the medical field, a method of collecting nucleic acids without any complicated procedure or the use of an organic solvent is preferred.

For methods of collecting nucleic acids other than the Boom method, WO 92/18514 and Japanese National-Phase Publication No. 2013-505719 disclose a method of collecting nucleic acids without using an organic solvent. WO 92/18514 discloses a method of adsorbing nucleic acids on alpha aluminum oxide particles, zirconia particles, titania particles, or the like and collecting the nucleic acids efficiently. Japanese National-Phase Publication No. 2013-505719 discloses a method of adsorbing and collecting nucleic acids by use of the principle of ion exchange chromatography and describes that aluminum oxide can be used as the material for anion-exchange.

On the other hand, Japanese National-Phase Publication No. 2005-505269 describes that nucleic acids can be bonded strongly to alpha aluminum oxide and gamma aluminum oxide, and conversely that the bond can be prevented, depending on the solution in which the nucleic acids are dissolved. Japanese National-Phase Publication No. 2005-505269 also describes that the bonded nucleic acids are rarely eluted even after repeated washing.

As mentioned above, while WO 92/18514 or Japanese National-Phase Publication No. 2013-505719 describes that aluminum oxide can be used to collect nucleic acids efficiently, Japanese National-Phase Publication No. 2005-505269 describes that the bonded nucleic acids are not eluted. We examined the method of collecting nucleic acids disclosed in WO 92/18514 which uses aluminum oxide.

In Comparative Example 1 which will be described later, aluminum oxide having a composition as close to that of Example 4 in WO 92/18514 as possible was prepared, and a nucleic acid was adsorbed by reference to the conditions in WO 92/18514. The adsorbed nucleic acid was then eluted, and we examined whether the nucleic acid was collected or not. Although the nucleic acid was adsorbed on the aluminum oxide, the elution ratio of the nucleic acid was low, and thus the nucleic acid could not be collected with a high yield.

Considering those results, we concluded that it could be helpful if a nucleic acid(s) can be collected efficiently in an easy method without using an organic solvent if the elution ratio of the nucleic acid(s) bound to the aluminum oxide is improved.

SUMMARY

We discovered that the nucleic acid elution ratio can be improved without a decrease in the nucleic acid adsorption ratio by adsorbing a water-soluble neutral polymer on the surface of aluminum oxide. We further discovered that the use of our method allows for the efficient collection of a very short nucleic acid such as miRNA as well.

We thus provide:

(1) A method of collecting a nucleic acid(s) from a biological sample, comprising the following steps:

step a) of mixing an aluminum oxide support with a water-soluble neutral polymer adsorbed on the surface thereof and a solution containing a nucleic acid(s), thereby adsorbing the nucleic acid(s) to the support, step b) of separating the support on which the nucleic acid(s) is/are adsorbed from the solution mixed in the step a), and step c) of collecting the nucleic acid(s) by adding an eluent to the support on which the nucleic acid(s) is/are adsorbed and which is separated in the step b).

(2) The method of collecting a nucleic acid(s) according to (1), wherein the water-soluble neutral polymer is a polymer having a zeta potential of not less than −10 mV and not more than +10 mV in a solution of pH7.

(3) The method of collecting a nucleic acid(s) according to (1) or (2), wherein the polymer is polyethylene glycol, polyvinylpyrrolidone, poly(2-ethyl-2-oxazoline) or hydroxypropyl methylcellulose.

(4) The method of collecting a nucleic acid(s) according to any one of (1) to (3), wherein the eluent is a buffer solution.

(5) The method of collecting a nucleic acid(s) according to any one of (1) to (4), wherein the biological sample is blood, urine, saliva, a mucous membrane, sweat, a cultured cell, a culture solution of cultured cells, or a tissue sample or specimen.

(6) A support for collecting a nucleic acid(s), in which a water-soluble neutral polymer is adsorbed on the surface of an aluminum oxide support.

(7) The support according to (6), wherein the water-soluble neutral polymer is a polymer having a zeta potential of not less than −10 mV and not more than +10 mV in a solution of pH7.

(8) The support according to (6) or (7), wherein the water-soluble neutral polymer is polyethylene glycol, polyvinylpyrrolidone, poly(2-ethyl-2-oxazoline) or hydroxypropyl methylcellulose.

(9) The support according to any one of (6) to (8), wherein the water-soluble neutral polymer is adsorbed to cover not less than 7% of the surface of the aluminum oxide support.

(10) A kit for collecting a nucleic acid(s), comprising the support according to any one of (6) to (9) and a buffer solution.

We provide for the high-yield collection of a nucleic acid(s) in an easy method without using an organic solvent even when aluminum oxide is used as a support, and further the high-yield collection of even a very short nucleic acid(s) such as pre-miRNA or miRNA, which has been conventionally difficult to collect efficiently.

DETAILED DESCRIPTION

For the biological sample, any sample containing a nucleic acid(s) can be used. Examples of the nucleic acids include RNA, DNA, RNA/DNA (chimera) and artificial nucleic acids. Examples of DNA include cDNA, genome DNA, and synthetic DNA. Examples of RNA include total RNA, mRNA, rRNA, miRNA, siRNA, snoRNA, snRNA or non-coding RNA, precursors thereof, and synthetic RNA. Synthetic DNA and synthetic RNA can be produced artificially based on a predetermined base sequence (it may be either native sequence or non-natural sequence) by use of, for example, an automated nucleic acid synthesizer.

Examples of biological samples include, but are not limited to, cell-derived samples such as cultured cells, culture solutions of cultured cells, tissue samples and specimens, samples derived from microorganisms such as bacteria and viruses, samples derived from animals including humans such as body fluids and feces, and solutions containing a compound which has a biological function such as protein, sugar, lipid in addition to the nucleic acid(s). The biological sample is preferably a cultured cell or a body fluid, and further preferably blood. Examples of blood include whole blood, plasma, serum, and blood cells.

When the biological sample is a liquid sample such as a body fluid, our methods may be applied directly after the sample is collected, or a solution may be added after the sample is collected to dilute the liquid sample. When the biological sample is a solid sample such as a cell pellet or tissue fragment, the solid sample may be diluted with water or a buffer solution after being collected and then used.

The biological sample may be subjected to a treatment as explained below if necessary. The treatment is carried out because the nucleic acid(s) in a biological sample is/are often capsuled in a compound such as a cell membrane, a cell wall, a vesicle, a liposome, a micelle, a ribosome, a histone, a nuclear membrane, a mitochondrion, a virus capsid, an envelope, an endosome, and an exosome and because they often interact with each other. To collect a nucleic acid(s) with a better yield, a treatment for releasing a nucleic acid(s) from such compounds may be carried out.

Specifically, the following treatment may be performed to improve the collection efficiency of a nucleic acid(s) from a biological sample containing *Escherichia coli*. For example, a mixture solution of 0.2M of sodium hydroxide and 1% SDS may be added to the biological sample containing *E. coli* (alkaline denaturation method), or a 10% sarkosyl solution may be added to the biological sample containing *E. coli* (non-denaturation method by sarkosyl). Lysozyme may be added to these solutions. The sample may also be treated with proteinase K at 37° C. for one hour. Other methods also include a sonication.

To improve collection efficiency of a nucleic acid(s) from a yeast-containing biological sample, the following treatment may be performed on the biological sample. For example, after the biological sample may be treated with zymolyase commercially available from SEIKAGAKU CORPORATION, and then 10% SDS may be added.

To improve collection efficiency of a nucleic acid(s) from a cell-containing biological sample, the following treatment may be performed on the biological sample. For example, 1% SDS may be added. Other methods include adding 4M or more of guanidinium chloride, a guanidine thiocyanate salt, urea or the like. Sarkosyl may be added to this solution to form a solution of 0.5% or more. Mercaptoethanol may also be added to result in a concentration of 50 mM or more.

In the above procedures, an inhibitor of a degradative enzyme of a nucleic acid may be added to suppress the degradation of the nucleic acid contained in the biological sample. As an inhibitor of DNA-degrading enzymes, EDTA may be added in a concentration of 1 mM or less. Commercially available inhibitors of RNA-degrading enzymes such as RNasin Plus Ribonuclease Inhibitor (Promega Corporation), Ribonuclease Inhibitor (TAKARA BIO INC.), and RNase inhibitor (TOYOBO CO., LTD.) may be used.

When DNA and RNA are present together in a biological sample, they can be separated by phenol-chloroform extraction. For example, when phenol-chloroform extraction is performed under acidic conditions, RNA and DNA are separated into a water layer and a chloroform layer, respectively. Under the neutral conditions, RNA and DNA are distributed into a water phase. This nature can be utilized to select the conditions depending on the type of the desired nucleic acid(s). The above-mentioned chloroform may be replaced by p-bromoanisole.

In the phenol-chloroform extraction, a commercially available reagent, ISOGEN (registered trademark: NIPPON GENE CO., LTD.), TRIZOL (registered trademark: Life Technologies Japan Ltd.), RNAiso (TAKARA BIO INC.), or 3D-GENE (registered trademark) RNA extraction reagent from liquid sample kit (Toray Industries, Inc.) may be used.

A single step in the treatments described above can be performed alone, or combined with another step(s) of a different procedure(s). The concentration of the solution to be used may vary as appropriate.

As a solution containing a nucleic acid(s), a solution in which a nucleic acid(s), an artificial nucleic acid(s), or a nucleic acid(s) modified with a dye or a phosphoric group is/are dissolved can be used. When a biological sample is used, a liquid sample such as a body fluid or a diluted solution thereof, or a diluted solution of a solid sample such as a cell pellet or tissue fragment may be used. A solution obtained after the biological sample containing a liquid sample or a solid sample is subjected to any of the above-mentioned treatments may be directly used, or may be diluted as required. The solution to be used for dilution is not particularly limited, but a solution which is widely used with a solution containing a nucleic acid(s) such as water or a Tris-hydrochloric acid buffer solution is preferably used. A solution containing a nucleic acid(s) is preferably a biological sample in which 4M or more of guanidinium chloride, a guanidine thiocyanate salt, or urea is added.

The length of a nucleic acid(s) to be collected is not particularly limited, but preferably 1000 base pairs or less. Furthermore, nucleic acids of 300 base pairs or less, which were conventionally difficult to collect, can be also collected with a high yield, and pre-miRNAs and miRNAs of 100 base pairs or less can also be collected with a high yield.

We achieve high-yield collection of a nucleic acid(s) by using an aluminum oxide support with a water-soluble neutral polymer adsorbed on the surface thereof. The support is an aluminum oxide support with a water-soluble neutral polymer adsorbed on the surface thereof, which will be referred to as "the support" hereinafter.

The adsorption ratio of the nucleic acid(s) adsorbed on the support can be calculated as follows. The amount of the nucleic acid(s) in a solution containing a nucleic acid(s) is first calculated. The support and the solution containing a nucleic acid(s) are then mixed. The amount of the nucleic acid(s) in the mixture solution after the nucleic acid(s) is/are adsorbed on the support is calculated, and the difference from the amount of the nucleic acid(s) in the solution containing a nucleic acid(s) is obtained. The resulting value is used as the amount of the nucleic acid(s) adsorbed on the support, and the adsorption ratio of the nucleic acid(s) can be calculated by dividing the amount of the nucleic acid(s) adsorbed on the support by the amount of the nucleic acid(s) in the solution containing a nucleic acid(s).

The elution ratio of the nucleic acid(s) can be obtained as follows. An eluent is added to the support on which a nucleic acid(s) is/are adsorbed, and the amount of the nucleic acid(s) in the solution after the elution is calculated to obtain the elution amount of the nucleic acid(s). The elution ratio can be obtained by dividing this elution amount of the nucleic acid(s) by the above-calculated amount of the nucleic acid(s) adsorbed on the support.

The nucleic acid collection ratio is obtained by the multiplication of the adsorption ratio and the elution ratio which are calculated by the above methods.

Examples of methods of quantifying the amount of the nucleic acid(s) include a UV-vis absorbance measurement, a fluorescence measurement, a luminescence measurement, electrophoresis, PCR, RT-PCR, an analysis using a microarray, and an analysis using a sequencer. An unmodified nucleic acid can be measured for the absorbance at 260 nm to quantify the amount of the nucleic acid. In the case of a nucleic acid modified with a fluorescent dye, the fluorescence intensity derived from the fluorescent dye is compared with the fluorescence intensity of a solution of a known concentration, and thus the amount of the nucleic acid can be quantified. Moreover, the quantification is carried out by electrophoresis. The calculation method of the collection ratio by electrophoresis causes the sample after the collection procedure to migrate simultaneously with a sample of a known concentration. The gel is stained, and the densities of the bands are compared by the image analysis for the determination.

A polymer is a general name for compounds in which a large number of repeating units called monomer, which is a basic unit, are chained. The polymer used in the support includes both of a homopolymer consisting of one monomer and a copolymer composed of two or more monomers. A polymer having an arbitrary polymerization degree is included. Both of naturally-occurring polymers and synthetic polymer are also included.

The water-soluble neutral polymer used in the support is a polymer which has water-soluble property and the solubility in water is at least 0.0001 wt % or more, preferably 0.001 wt % or more, more preferably 0.01 wt % or more, and further preferably 0.1 wt % or more.

The water-soluble neutral polymer used in the support is a polymer having a zeta potential of not less than −10 mV and not more than +10 mV in a solution of pH7. More preferably, the water-soluble neutral polymer used in the support is a polymer having a zeta potential of not less than −8 mV and not more than +8 mV, further preferably not less than −6 mV and not more than +6 mV, and particularly preferably not less than −4.0 mV and not more than +1.1 mV.

The zeta potential is one value indicating electrical properties on colloid interfaces in a solution. When charged colloids are dispersed in a solution, on the surface of a colloid, an electrical double layer is formed by counter ions with respect to the charge of the colloid surface. The electrical potential on this colloid surface is called surface potential. Because the electrical double layer is formed by static interaction due to the surface charge of the colloid, ions are more strongly fixed as they are closer to the colloid. In the electrical double layer, a layer where counter ions are strongly fixed to the colloid surface due to the static interaction is called a stern layer, and the potential of fixed layer is called stern potential. When colloids are caused to move in the solution, the fixed layers also move with the colloids. When this happens, outside the stern layer viewed from a colloid, there is a boundary surface that moves together with the colloid due to the viscosity of the solution. This surface is called slipping plane. The potential of this slipping plane is defined as zeta potential with the potential of a point sufficiently far from the colloid as point zero. Thus, the zeta potential varies depending on the surface charge of colloids. Since the surface charge changes according to protonation and deprotonation which depend on pH, the value in a solution of pH7 is used as a standard. Because the distance from the colloid to the slipping plane is generally small compared to the colloid size, the colloid surface and the slipping plane can be represented approximately. In the case of the water-soluble neutral polymer as well, the surface potential of colloids dispersed in the solution can be considered as the zeta potential.

The zeta potential can be obtained by use of electrokinetic phenomenon such as electrophoresis, electro-osmosis, back flow potential, and sedimentation potential, and can be measured by a method such as a microscopic electrophoresis method, an electrophoresis method using a rotating diffraction grating method, a laser Doppler electrophoresis method, an ultrasonic vibration potential method, and an electroacoustic method. These measurements can be performed using a zeta potential measurement instrument. The zeta potential measurement instruments are commercially available from, for example, Otsuka Electronics Co., Ltd., Malvern Instruments Ltd., Ranku Brother Ltd., and PenKem Inc.

Any of the above instruments can be used to measure the zeta potential, but the laser Doppler electrophoresis method is common. The laser Doppler electrophoresis method is a measurement method which utilizes the Doppler effect which is the change in the frequency of light or sound waves when the light or sound waves strike an object in motion due to electrophoresis, and scatter or reflect.

When the zeta potential of a polymer is measured, a polymer solution can be prepared as a colloid dispersion to measure the zeta potential. For example, a polymer is dissolved in an electrolyte such as a phosphate buffer solution, a sodium chloride solution, and a citrate buffer solution to form a polymer solution, and scattered light and reflected light of the polymer scattered in the solution are detected for the measurement. A bigger colloid size allows for the detection of scattered light and reflected light under a lower concentration.

Specific conditions for measuring the zeta potential of a polymer by the laser Doppler method are not particularly limited, but the zeta potential of the polymer can be measured as follows, for example: the polymer is dissolved in a phosphate buffer solution (10 mM, pH7) under the concentration of not less than 1 wt % and not more than 10 wt %; this solution is then placed in a cell for measurement and installed in a zeta potential measurement instrument which utilizes the principle of the laser Doppler electrophoresis method, and thus the zeta potential can be measured at room temperature. As the zeta potential measurement instrument, for example, ELS-Z manufactured by Otsuka Electronics Co., Ltd., can be used.

Examples of the water-soluble neutral polymer used in the support include the following. For example, a polyvinyl polymer such as polyvinyl alcohol or polyvinylpyrrolidone, a polyacrylamide polymer such as polyacrylamide, poly(N-isopropylacrylamide) or poly(N-(hydroxymethyl)acrylamide, a polyalkylene glycol polymer such as polyethylene glycol, polypropylene glycol, or polytetramethylene ether glycol, or a cellulose such as poly(2-ethyl-2-oxazoline), (hydroxypropyl)methyl cellulose, methyl cellulose, ethyl cellulose, 2-hydroxyethyl cellulose, or hydroxypropyl cellulose or the like can be used. Copolymers containing the above polymer can be also used.

Other examples of the water-soluble neutral polymer used in the support also include polysaccharides or polysaccharide analogs such as ficoll, agarose, chitin and dextran as well as proteins and peptides such as albumin.

A part of a functional group of the water-soluble neutral polymer may be ionized or substituted with a functional group showing positivity or negativity. A functional group exhibiting solubility in water such as an acetyl group may be introduced to side chains.

The molecular weight of the water-soluble neutral polymer is, for example, preferably 0.4 kD or more, and more preferably, 6 kD or more.

The aluminum oxide used in the support is an amphoteric oxide expressed by the composition formula, $Al_2O_3$ and is also known as alumina.

For the aluminum oxide, naturally-produced aluminum oxide or aluminum oxide manufactured industrially may be used. Examples of methods of producing aluminum oxide include the Bayer method in which gibbsite is used as a starting material, an alkoxide method via a hydroxide in the form of boehmite (also called sol-gel method), a neutralization method, an oil droplet method, an aluminum salt thermal decomposition method, and an anodic oxidation method.

Aluminum oxide manufactured industrially can be available from reagent manufacturers, catalyst chemical manufacturers, the Committee of Reference Catalyst of the Catalysis Society of Japan, and the like.

Depending on the crystal structure, aluminum oxide is classified as alpha aluminum oxide, rho aluminum oxide, khi aluminum oxide, kappa aluminum oxide, eta aluminum oxide, gamma aluminum oxide, delta aluminum oxide, theta aluminum oxide, or the like. Gamma aluminum oxide with a high specific surface area is preferred.

Aluminum oxide changes its acid sites ($AL^+$, $Al-OH_2^+$) and basic sites ($Al-O^-$) depending on the calcination temperature during the production. Depending on the number of acid sites and basic sites of the aluminum oxide, the aluminum oxide is classified as acidic alumina if there are more acid sites, as basic alumina if there are more basic sites, and as neutral alumina if the acid sites and the basic sites are almost equal. The difference in this property can be confirmed by the addition of a pH indicator, i.e., BTB solution. When a BTB solution is added, if the aluminum oxide turns yellow, the aluminum oxide is acidic alumina; if the aluminum oxide turns green, it is neutral alumina; and if the aluminum oxide turns blue, it is basic alumina. Any aluminum oxide can be used regardless of such a difference in property.

Aluminum oxide is preferably in a granular form. The particle size may be the same, or different particle sizes can be combined in use. For example, the aluminum oxide having a particle size of less than 212 µm can be preferably used, more preferably the aluminum oxide having a particle size of less than 100 µm can be used.

The particle size is defined by an aperture size of a sieve based on JIS Z-8801-1:2006 according to Japanese Industrial Standards. For example, in the aperture size according to the above JIS standard, particles which can pass through the sieve of 40 µm and cannot pass through the sieve of 32 µm will have the particle size of not less than 32 µm and less than 40 µm.

The eluent is not particularly limited as long as the nucleic acid(s) adsorbed on the support can be eluted, but is preferably a buffer solution, and the buffer solution may contain a chelating agent. Specific examples thereof include a citrate buffer solution containing citric acid and sodium citrate, a phosphate buffer solution containing phosphoric acid and sodium phosphate, and a Tris-EDTA buffer solution obtained by adding EDTA to a Tris-hydrochloric acid buffer solution containing tris hydroxy aminomethane and hydrochloric acid.

The pH of the buffer solution is preferably pH4 or more and pH9 or less, and more preferably pH5 or more and pH8 or less.

The buffer solution can be prepared as follows. For example, a 0.5M phosphate buffer solution (pH7) is prepared as follows. A 0.5M aqueous solution of disodium hydrogen phosphate and 0.5M sodium dihydrogen phosphate are prepared. While measuring the pH, a sodium dihydrogen phosphate solution is added to the 0.5M aqueous solution of disodium hydrogen phosphate until the pH reaches pH7. In a similar way, buffer solutions of other pH can be also prepared.

For a chelating agent contained in the buffer solution, a substance that has a ligand having several coordination positions, and binds to a metal ion to form a complex can be used.

Specific examples of chelating agents include ethylenediaminetetraacetic acid (EDTA), nitrilotriacetic acid (NTA), glycol ether diamine tetraacetic acid (EGTA), polyphosphoric acid, metaphosphoric acid and/or salts thereof. The final concentration of the chelating agent is not particularly limited as long as it is 50 mM or more, and is preferably 100 mM or more, and further preferably 500 mM or more.

Examples of compounds as a chelating agent other than the above include anionic polymers. Since a polymer which has carboxylic acid on the side chains coordinate to a metal ion, the buffer solution may contain such a polymer. Examples of polymers having such a function include polyvinyl sulfonic acid and/or salt thereof. The final concentration is not particularly limited as long as it is 1 wt % or more, and preferably 10 wt % or more.

Our method of collecting a nucleic acid(s) from a biological sample comprises a step a) of mixing an aluminum oxide support with a water-soluble neutral polymer adsorbed on the surface thereof and a solution containing a nucleic acid(s) to adsorb the nucleic acid(s) to the support, a step b) of separating the support on which the nucleic acid(s) is/are adsorbed from the solution mixed in the step a), and a step c) of adding an eluent to the support on which the nucleic acid(s) is/are adsorbed in the step b) to collect the nucleic acid(s). Each step will be explained in detail below.

The support is produced by adsorbing a water-soluble neutral polymer onto the surface of aluminum oxide. The surface coverage ratio of the polymer is preferably 7% or more, more preferably 10% or more, further preferably 20% or more, particularly preferably 30% or more, and the most preferably 40% or more. The water-soluble neutral polymer may not be necessarily adsorbed in an even thickness.

The coverage ratio of the polymer on alumina is calculated by analyzing a potential map obtained from a surface potential microscope (also known as Kelvin probe force microscope; KFM). For the surface potential microscope, for example, NanoScope Iva AFM Dimension 3100 Stage AFM System manufactured by Digital Instruments of Bruker AXS can be used.

When the surface coverage ratio is calculated by use of the surface potential microscope, the scale of the field of the view is 0.5 µm×1 µm. The surface coverage ratio is calculated as follows. First, the surface potential image of the aluminum oxide is obtained to calculate the average potential in the field of the view. The surface potential image of the water-soluble neutral polymer is obtained to calculate the average potential in the field of the view. The surface potential image of the aluminum oxide on which the water-soluble neutral polymer is adsorbed is then obtained to calculate the average potential in the field of the view. The coverage ratio of the aluminum oxide alone is considered as 0% and that of the water-soluble neutral polymer alone is considered as 100%. The ratio of the average potential of the aluminum oxide on which the water-soluble neutral polymer is adsorbed to that of the water-soluble neutral polymer is obtained, and thus the surface coverage ratio of the aluminum oxide on which the water-soluble neutral polymer is adsorbed is calculated. When the surface coverage ratio is calculated, for the average potential in each field of view to be used, three single particles are selected randomly, and each average value of measured values is used.

Photoshop manufactured by Adobe Systems Incorporated can be used as an image analysis software when the surface coverage ratio is calculated. In the image analysis, the average value of the surface potential of the aluminum oxide is used as a lower limit of the scale, and the average value of the surface potential of the water-soluble neutral polymer is used as an upper limit of the scale. The lower limit color is set with black (8 bits, RGB value 0), and the upper limit color is set with red (R value 255), green (G value 255), blue (B value 255), or the like. The surface potential image of the aluminum oxide on which the water-soluble neutral polymer is adsorbed is displayed in the scale set as above, and either the R value, the G value, or the B value is divided by 255, and the ratio is used as the surface coverage ratio.

Before the water-soluble neutral polymer is adsorbed on the surface, the aluminum oxide may be washed in advance with a solution such as water or ethanol to remove the impurities adsorbed on the surface, or this washing step may be omitted.

Examples of methods of adsorbing the water-soluble neutral polymer on the surface of the aluminum oxide include a method in which the water-soluble neutral polymer is dissolved to prepare a water-soluble neutral polymer solution and bringing the solution into the contact with the aluminum oxide. Specifically, the aluminum oxide may be dipped in the water-soluble neutral polymer solution, the water-soluble neutral polymer solution may be added dropwise to the aluminum oxide, the water-soluble neutral polymer solution may be coated on the aluminum oxide, the water-soluble neutral polymer solution may be sprayed onto the aluminum oxide in the form of a mist.

The methods of dipping the aluminum oxide in the water-soluble neutral polymer solution are not particularly limited. For example, it may be stirred by pipetting or mixing by inversion, or by a disperser such as a stirrer, mixer, vortex or a mill, a sonication instrument or the like.

The concentration of the water-soluble neutral polymer is not particularly limited, but preferably 0.01 wt % or more, and more preferably, 0.1 wt % or more.

The mixing time for stirring is not particularly limited as long as the water-soluble neutral polymer and the aluminum oxide are mixed evenly, but in a vortex, it is stirred for 1 minute or more, and preferably 5 minutes or more.

The water-soluble neutral polymer can also be dip-coated on the aluminum oxide using a sifter or a sieve. The mixing time for dipping in the solution may be, in a polymer concentration of 0.1 wt % or more, 5 minutes or more, and preferably 30 minutes or more.

When the water-soluble neutral polymer solution is added dropwise, a dropper, a dropping funnel or the like can be used. When the polymer solution is added dropwise, the aluminum oxide may also be shaken or rotated, or a spin coater or the like may be used.

When the water-soluble neutral polymer solution is coated, a brush, roller or a wire bar can be used.

When the water-soluble neutral polymer solution is sprayed in a form of a mist, an air spray, an air brush or the like can be used.

After the water-soluble neutral polymer is adsorbed on the aluminum oxide in the methods described above, a centrifugation may be carried out to remove the supernatant polymer solution, or the aluminum oxide is directly used for nucleic acid collection without centrifugation. When the polymer solution is dissolved in a solvent, after the water-soluble neutral polymer is adsorbed on the aluminum oxide and the solvent is removed, it may be dried or may be used directly to collect a nucleic acid(s) without drying.

The resulting support may be preserved and then used, or prepared at time of use.

When the obtained water-soluble neutral polymer is solid, the water-soluble neutral polymer solution can be prepared by dissolving the polymer in water or an organic solvent, and when the obtained water-soluble neutral polymer is a solution, the water-soluble neutral polymer solution may be prepared by diluting the solution. When it is hard to dissolve the polymer or mix the polymer due to the high viscosity of the solution, a heating treatment or sonication may be performed. Examples of organic solvent include ethanol, acetonitrile, methanol, propanol, tert-butanol, DMF, DMSO, acetone, ethylene glycol and glycerol. It is preferred that solvents compatible with water are used. When the polymer is poorly soluble in water, any of the above organic solvents may be added.

A support produced by binding covalently the aluminum oxide and the water-soluble neutral polymer by, for example, a linker molecule is not the support. Specific examples of linker molecules include silane coupling agents.

The step a) is a step of mixing the support prepared according to the above preparation method with a solution containing a nucleic acid(s), and adsorbing the nucleic acid(s) to the support. The method of mixing the support and the solution containing a nucleic acid(s) is not particularly limited but, for example, may be carried out by pipetting or mixing by inversion, or an instrument such as a mixer or vortex may be used. The mixing time is not particularly limited, and may be about 5 minutes, or for a longer time. The support may be packed in a column to cause a solution containing a nucleic acid(s) to pass through the column.

The step b) is a step of separating the support on which the nucleic acid(s) is/are adsorbed from the mixture mixed in the step a). Examples of separation methods include a method in which the mixture resulting from the step a) is centrifuged, the support on which the nucleic acid(s) is/are adsorbed precipitates, and then the supernatant is removed. Since the relative density of the support on which the nucleic acid(s) is/are adsorbed is higher than that of water, the precipitation can be done easily by the centrifugation. Conditions for centrifugation may be a treatment at 6000 G for 1 minute, and more preferably a treatment at 10000 G for 1 minute. Other separation methods include a method in which an ultrafiltration membrane is used. The mixture obtained from the step a) is passed through an ultrafiltration membrane having a smaller pore diameter than the particle size of the support on which the nucleic acid(s) is/are adsorbed, and thus the support on which the nucleic acid(s) is/are adsorbed is separated. Such an ultrafiltration membrane is available in a kit, and a centrifugal filter kit represented by ULTRAFREE (registered trademark) manufactured by Merck Ltd., or NANOSEP (registered trademark) manufactured by Pall Corporation can be obtained for use.

As required, the following treatment may be further performed after the procedure of the step b) because it is possible that biological sample-derived material other than the nucleic acid(s) of interest is adsorbed on the surface of the support after the step a). For example, to isolate the nucleic acid(s) with higher purity, treatment such as washing or degradation may be performed. Specific examples thereof include various treatments such as washing with water to remove non-specifically adsorbed compounds, washing with a surfactant to remove non-specifically adsorbed proteins, washing with a surfactant-containing solution to remove ions and low-molecular compounds, washing with an organic solvent to remove non-specifically adsorbed hydrophobic compounds, adding a protein-degrading enzyme to degrade non-specifically adsorbed proteins, adding an RNA-degrading enzyme to isolate only DNA, and adding an DNA-degrading enzyme to isolate only RNA.

The step c) is a step of collecting the nucleic acid(s) by adding an eluent to the support on which the nucleic acid(s) is/are adsorbed and which is separated in the step b).

In the addition of the above eluent to collect the nucleic acid(s), when the support and the solution in which the nucleic acid(s) is/are eluted are separated, example methods thereof include a method of, in the step c), centrifuging the mixture obtained by adding the eluent to the support on which the nucleic acid(s) is/are adsorbed to precipitate the support, and obtaining the supernatant in which the nucleic acid(s) is/are eluted. Since the relative density of the support is greater than that of water, the precipitation can be done easily by the centrifugation. Conditions for centrifugation may be a treatment at 6000 G for 1 minute, and preferably a treatment at 10000 G for 1 minute.

Other separation methods include a method in which an ultrafiltration membrane is used. The mixture obtained from the step c) is passed through an ultrafiltration membrane having a smaller pore diameter than the particle size of the support, and thus the support is separated. Such an ultrafiltration membrane is available in a kit, and a centrifugal filter kit represented by ULTRAFREE (registered trademark) manufactured by Merck Ltd., or NANOSEP (registered trademark) manufactured by Pall Corporation can be obtained for use.

A nucleic acid(s) thus collected can be chemically modified as necessary. Examples of chemical modifications include, with regard to the nucleic acid termini, fluorescent dye modification, quencher modification, biotin modification, amination, carboxylation, maleinimidation, succinimidation, phosphorylation and dephosphorylation. Other examples include staining by an intercalator. These modifications may be introduced by chemical reaction, or may be introduced by enzyme reaction. The nucleic acid(s) can be quantified indirectly by introducing these modification groups before the above quantification and quantifying the modification groups introduced via chemical modification instead of quantifying the nucleic acid(s). Since our methods allow a nucleic acid(s) to be collected, and especially a short-chain nucleic acid(s) to be collected with a high yield, sensitive quantification is possible in the above quantification.

The kit for collecting a nucleic acid(s) can be used to collect a nucleic acid(s) from a biological sample efficiently. The kit for collecting a nucleic acid(s) includes the support and a buffer solution as its constituent components. The kit may further include instructions in addition.

The kit for collecting a nucleic acid(s) may contain the support in a dry condition, or with the support dipped in a solution of a water-soluble neutral polymer.

As the buffer solution included in the kit for collecting a nucleic acid(s), a buffer solution which can be used as the eluent in the above step c) may be utilized.

EXAMPLES

Our methods will be more specifically explained by way of the following Examples.

Materials and Methods

Polyethylene glycol was purchased from Merck Ltd., poly(2-ethyl-2-oxazoline) was purchased from Alfa Aesar, A Johnson Matthey Company, a basic gamma aluminum oxide (N613N) was purchased from JGC Catalysts and Chemicals Ltd., and alpha aluminum oxide (CAS. No 1344-28-1, Cat. 013-23115), acidic gamma aluminum oxide (CAS. No 1344-

28-1, Cat. 590-13685) and neutral gamma aluminum oxide (CAS. No 1344-28-1, Cat. 013-590-13715) were purchased from Wako Pure Chemical Industries, Ltd. The aqueous polymer solutions used in Examples were obtained by dissolving polymers in water to each concentration. In the Examples, unless otherwise specified, basic gamma aluminum oxide was used. Furthermore, unless otherwise specified, the aluminum oxide was used in the experiments directly after the purchase without a sieving process or the like.

A 100 bp DNA ladder (Fragments; 200 bp, 300 bp, 1000 bp) was purchased from TAKARA BIO INC., and ethidium bromide was purchased from NACALAI TESQUE, INC. Synthesized products obtained by converting a 22-base nucleic acid known as the let7a sequence into a DNA sequence and into RNA sequence respectively were purchased from Eurofins Genomics Company. Hereinafter, a synthetic nucleic acid of an RNA sequence will be described as RNA22, and a synthetic nucleic acid of a DNA sequence as DNA22. These nucleic acids were directly used without any particular purification.

Other agents were purchased from Wako Pure Chemical Industries, Ltd., Tokyo Chemical Industry Co., Ltd., and Sigma-Aldrich Japan, and used directly without any particular purification.

CUTE MIXER CM-1000 manufactured by TOKYO RIKAKIKAI CO, LTD was used as a mixer, and Nanodrop 3300 manufactured by Thermo Fisher Scientific and FLUO-ROMAX-3 manufactured by HORIBA, Ltd. were used as fluorometers, ELS-Z manufactured by Otsuka Electronics Co., Ltd. was used for the measurement of zeta potential, and Mupid-eXU manufactured by ADVANCE CO., LTD. was used for electrophoresis. For a sieve, MVS-1 manufactured by AS ONE Corporation was used. Stained agarose gel was analyzed using Typhoon 9410 manufactured by GE Healthcare Japan Corporation. For image analysis of the agarose gel, IMAGEQUANT (registered trademark) manufactured by Molecular Dynamics was used. NanoScope Iva AFM Dimension 3100 Stage AFM System manufactured by Digital Instruments of Bruker AXS was used as a Kelvin probe force microscope.

Photoshop manufactured by Adobe Systems Incorporated was also used as an image analysis software to calculate the surface coverage ratio. In the image analysis, the average value of the surface potential of the aluminum oxide was used as a lower limit of the scale, and the average value of the surface potential of the water-soluble neutral polymer was used as an upper limit of the scale. The lower limit color was set with black (8 bits, RGB value 0), and the upper limit color was set with red (R value 255), green (G value 255), or blue (B value 255). In the scale set as above, the surface potential image of the aluminum oxide with the water-soluble neutral polymer adsorbed was displayed, and either the R value, the G value, or the B value was divided by 255 to use the ratio as the surface coverage ratio.

When the surface coverage ratio is calculated by use of the surface potential microscope, the scale of the field of the view is 0.5 μm×1 μm. The surface coverage ratio was calculated as follows. First, the surface potential image of the aluminum oxide was obtained to calculate the average potential in the field of the view. The surface potential image of the water-soluble neutral polymer was obtained to calculate the average potential in the field of the view. The surface potential image of the aluminum oxide with the water-soluble neutral polymer adsorbed was then obtained to calculate the average potential in the field of the view. With the coverage ratio of the aluminum oxide alone as 0% and that of the water-soluble neutral polymer alone as 100%, the ratio of the average potential of the aluminum oxide on which the water-soluble neutral polymer was adsorbed to that of the water-soluble neutral polymer was obtained, and the surface coverage ratio of the aluminum oxide on which the water-soluble neutral polymer was adsorbed was thus calculated. When the surface coverage ratio was calculated, for the average potential in each field of view to be used, three single particles were selected randomly, and the average value of measured values of each was used.

Comparative Example 1 Collection of a Nucleic Acid Using a Support in which a Water-Soluble Neutral Polymer is not Adsorbed on the Surface Basic gamma aluminum oxide (N613N, JGC Catalysts and Chemicals Ltd.) having a similar composition as the aluminum oxide A disclosed in WO 92/18514 (Example 4, Table 2), and alpha aluminum oxide (Wako Pure Chemical Industries, Ltd.) having a similar composition as the aluminum oxide D disclosed in the same document (Example 4, Table 2) were used to examine if a nucleic acid could be collected efficiently or not. As an eluent for eluting nucleic acids adsorbed on the aluminum oxide, WO 92/18514 and Japanese National-Phase Publication No. 2013-505719 disclose that a phosphate buffer solution or a Tris-EDTA buffer solution may be used. Since Japanese National-Phase Publication No. 2005-505269 discloses that a phosphoric acid solution inhibits the binding of nucleic acids with the aluminum oxide, a phosphate buffer solution (0.5M, pH8) or a Tris-EDTA buffer solution (0.5M Tris, 0.5M EDTA, pH8) was used as an eluent to perform the following experiment.

First, 0.5 mg of alpha aluminum oxide or gamma aluminum oxide was measured out and added to a 1.5-ml tube. To each tube was added 200 μl of ethanol, and each resulting mixture was vortex-mixed and centrifuged for 1 minute by a centrifuge, and then the supernatant was removed. This procedure was further repeated twice to carry out the washing.

Then, 100 μl of a 6M aqueous solution of a guanidine thiocyanate salt in which 100 pmol of DNA22 was dissolved was added to these, and stirred in a mixer for 5 minutes. The resulting mixtures were centrifuged (10000 G, 1 min) and, after the supernatant was removed and 100 μl of a 0.05% Tween solution was added, vortex-mixed. This procedure was further repeated twice. Afterwards, 50 μl of a phosphate buffer solution (0.5M, pH8) or a Tris-EDTA buffer solution (0.5M Tris, 0.5M EDTA, pH8) was added, and the resulting mixtures were stirred in a mixer for 5 minutes. The resulting mixtures were centrifuged by a centrifuge (10000 G, 1 min) to collect a nucleic acid solution.

The adsorption ratio was calculated by the fluorescence measurement of the Cy3 as follows. First, 100 μl of the 6M aqueous solution of a guanidine thiocyanate salt in which 100 pmol of DNA22 was dissolved before the alpha aluminum oxide and gamma aluminum oxide were added was measured for the fluorescence intensity, and then the fluorescence intensity after alpha aluminum oxide and gamma aluminum oxide were added and mixed was measured. The fluorescence intensity after the aluminum oxide was added was divided by the fluorescence intensity before the aluminum oxide was added, and the quotient was multiplied by the amount of the nucleic acid (100 pmol) before the addition to calculate the amount of the nucleic acid in the solution. The difference between the amount of the nucleic acid (100 pmol) before the addition, and this value was taken to calculate the amount of the adsorbed nucleic acid. The amount of the adsorbed nucleic acid was divided by the amount of the nucleic acid (100 pmol) before the aluminum oxide was added to calculate the adsorption ratio.

The elution ratio was calculated by the fluorescence measurement of the Cy3 as follows. To the aluminum oxide on which the nucleic acid was adsorbed was added 50 µl of a phosphate buffer solution or a Tris-EDTA buffer solution individually, and a fluorescence measurement was performed on the eluates after the elution. Then 50 µl of a phosphate buffer solution and a Tris-EDTA buffer solution in which 100 pmol of DNA22 was dissolved were prepared, and the fluorescence measurement was performed on each solution. The fluorescence intensity of the eluates was divided by the fluorescence intensity of these solutions, and the amount of the eluted nucleic acid was calculated. The amount of the eluted nucleic acid was divided by the amount of the adsorbed nucleic acid to calculate the elution ratio. The collection ratio was calculated by multiplying the obtained adsorption ratio by the elution ratio. Results are shown in Table 1.

These results showed that the method of collecting the nucleic acid using gamma aluminum oxide or alpha aluminum oxide in which the polymer was not adsorbed on the surface as the support resulted in a low elution ratio and a low nucleic acid collection ratio.

TABLE 1

| Aluminum Oxide Without Polymer Attached | Eluent | Adsorption Ratio [%] | Elution Ratio [%] | Collection Ratio [%] |
|---|---|---|---|---|
| Gamma Aluminum Oxide | Phosphate Buffer Solution | 92 | 4.1 | 3.8 |
|  | Tris-EDTA Buffer Solution | 97 | 5.5 | 5.4 |
| Alpha Aluminum Oxide | Phosphate Buffer Solution | 23 | 15 | 3.5 |
|  | Tris-EDTA Buffer Solution | 22 | 21 | 4.7 |

Comparative Example 2 Preparation of Aluminum Oxide Supports with Water-Soluble Polymers Different than a Water-Soluble Neutral Polymer Adsorbed on the Surface Thereof First, 0.5 mg of gamma aluminum oxide was measured out and added to 1.5-ml tubes. As a polymer solution, polyacrylic acid (PAcA, 5.1 kD, 10 wt %), dextran sulfate (DS, 4 kD, 10 wt %), polyvinyl sulfonic acid (PVSA, 10 wt %), polyallylamine (PAA, 17 kD, 10 wt %), and poly-L-lysine (PLL, 150 kD, 1 wt %) were added to these tubes respectively in an amount of 50 µl for each, and the mixtures were stirred for 10 minutes in a mixer. The mixtures were centrifuged by a centrifuge (10000 G, 1 min), and the supernatant was removed. Gamma aluminum oxide with each polymer adsorbed on the surface thereof was thus obtained.

Comparative Example 3 Collection of a Nucleic Acid Using Aluminum Oxide with Each Water-Soluble Polymer Different than a Water-Soluble Neutral Polymer Adsorbed on the Surface Thereof as a Support Gamma aluminum oxide which was produced in 1.5-ml tubes in Comparative Example 2 and in which polyacrylic acid (PAcA, 5.1 kD, 10 wt %), dextran sulfate (DS, 4 kD, 10 wt %), polyvinyl sulfonic acid (PVSA, 10 wt %), polyallylamine (PAA, 17 kD, 10 wt %), or poly-L-lysine (PLL, 150 kD, 1 wt %) was adsorbed on the surface thereof as a water-soluble polymer different than a water-soluble neutral polymer was measured out in an amount of 0.5 mg and used as a support. The eluent was a Tris-EDTA buffer solution (0.5M Tris, 0.5M EDTA, pH8), and other conditions and procedures were carried out the same way as in Comparative Example 1, and the nucleic acid adsorption ratio, the nucleic acid elution ratio, and the nucleic acid collection ratio were calculated. Results are shown in Table 2.

These results showed that the use of gamma aluminum oxide with polyacrylic acid, polyvinyl sulfonic acid, and dextran sulfate adsorbed on the surface as supports resulted in a low nucleic acid adsorption ratio and elution ratio as well as a low nucleic acid collection ratio. When gamma aluminum oxide with polyallylamine and poly-L-lysine adsorbed on the surface thereof was used as supports, while the adsorption ratio of nucleic acid was maintained high, the elution ratio decreased and the collection ratio was also low.

Example 1 Preparation of Aluminum Oxide Supports with Water-Soluble Neutral Polymers Adsorbed on the Surface Thereof First, 0.5 mg of gamma aluminum oxide was measured out and added to 1.5-ml tubes. As an aqueous polymer solution, water-soluble neutral polymer, i.e., polyvinyl alcohol (11% acetylation, PVA, 18 kD, 10 wt %), poly(2-ethyl-2-oxazoline) (PEOz, 5 kD, 10 wt %), polyethylene glycol (PEG, 10 kD, 10 wt %), hydroxypropyl methylcellulose) (HPMC, 10 kD, 10 wt %), or polyvinylpyrrolidone (PVP, 10 kD, 10 wt %) was individually added in an amount of 50 µl to each tube. Other conditions and procedures were the same as in Comparative Example 2, and gamma aluminum oxide supports with each polymer adsorbed on the surface thereof were thus obtained.

Example 2 Collection of a Nucleic Acid Using Gamma Aluminum Oxide with Water-Soluble Neutral Polymers Adsorbed on the Surface Thereof as Supports Gamma aluminum oxide which was produced in Example 1 and in which polyvinyl alcohol (11% acetylation, PVA, 18 kD, 10 wt %), poly(2-ethyl-2-oxazoline) (PEOz, 5 kD, 10 wt %), polyethylene glycol (PEG, 10 kD, 10 wt %), hydroxypropyl methylcellulose) (HPMC, 10 kD, 10 wt %), or polyvinylpyrrolidone (PVP, 10 kD, 10 wt %) was adsorbed on the surface as each water-soluble neutral polymer was measured out in an amount of 0.5 mg, and used as a support. Other conditions and procedures were carried out the same way as in Comparative Example 3, and the nucleic acid adsorption ratio, elution ratio, and collection ratio were calculated. Results are shown in Table 2.

These results showed that, compared to Comparative Example 3, when gamma aluminum oxide with a water-soluble neutral polymer adsorbed on the surface thereof was used as a support, the nucleic acid adsorption ratio was maintained high, and the elution ratio and collection ratio improved.

TABLE 2

| Polymer Attached to Gamma Aluminum Oxide | Adsorption Ratio [%] | Elution Ratio [%] | Collection Ratio [%] | |
|---|---|---|---|---|
| PAcA | 11 | 14 | 1.5 | Comparative Example 3 |
| DS | 74 | 7.5 | 5.6 | Comparative Example 3 |
| PVSA | 12 | 22 | 2.7 | Comparative Example 3 |
| PVA | 81 | 78 | 63 | Example 2 |
| PEOz | 91 | 90 | 82 | Example 2 |
| PEG | 98 | 86 | 84 | Example 2 |
| HPMC | 77 | 88 | 68 | Example 2 |
| PVP | 76 | 92 | 70 | Example 2 |
| PAA | 95 | 12 | 11 | Comparative Example 3 |
| PLL | 85 | 1.6 | 1.4 | Comparative Example 3 |

Comparative Example 4 Measurement of the Zeta Potential of Water-Soluble Polymers Different than a Water-Soluble Neutral Polymer Water-soluble polymers different than a water-soluble neutral polymer and used in Comparative Example 3, i.e., polyacrylic acid (PAcA, 5.1 kD), dextran sulfate (DS, 4 kD), polyvinyl sulfonic acid (PVSA), polyallylamine (PAA, 17 kD), and poly-L-lysine (PLL, 150 kD) were individually dissolved in a phosphate buffer solution (10 mM, pH7) such that the final concentration would be not less than 1 wt % and not more than 10 wt %, and measured for the zeta potential, using ELS-Z manufactured by Otsuka Electronics Co., Ltd. Results are shown in Table 3. In Table 3, the zeta potential obtained in this measurement and the collection ratio of DNA22 when the gamma aluminum oxide with each polymer adsorbed on the surface thereof was used as a support (results of Comparative Example 3) are correlated, and polymers were ordered in the ascending order of the zeta potential values.

These results showed that the zeta potential of the water-soluble polymers different than water-soluble neutral polymers which were used in Comparative Example 3 was not more than −17 mV or not less than +11 mV.

Example 3 Measurement of the Zeta Potential of Water-Soluble Neutral Polymers

Water-soluble neutral polymers used in Example 2, i.e., polyvinyl alcohol (11% acetylation, PVA, 18 kD), poly(2-ethyl-2-oxazoline) (PEOz, 5 kD), polyethylene glycol (PEG, 10 kD), hydroxypropyl methylcellulose (HPMC, 10 kD), and polyvinylpyrrolidone (PVP, 10 kD) were individually dissolved in a phosphate buffer solution (10 mM, pH7) such that the final concentration would be not less than 1 wt % and not more than 10 wt %, and measured for the zeta potential in the same way as in Comparative Example 4.

In Table 3, the zeta potential obtained in this measurement and the collection ratio of DNA22 when the gamma aluminum oxide with the polymer adsorbed on the surface thereof was used as supports (results of Example 2) are correlated, and polymers were ordered in the ascending order of the zeta potential values.

These results showed that the zeta potential of the water-soluble neutral polymers which improved the nucleic acid collection ratio in Example 2 was not less than −4 mV and not more than +1.1 mV in a solution of pH7, and the collection ratio further improved compared to the water-soluble polymers having the zeta potential of not more than −17 mV and not less than +11 mV.

TABLE 3

| Polymer Attached to Gamma Aluminum Oxide | Zeta Potential [mV] | Collection Ratio [%] | |
|---|---|---|---|
| PAcA | −37 | 1.5 | Comparative Example 4 |
| DS | −18 | 5.6 | Comparative Example 4 |
| PVSA | −17 | 2.7 | Comparative Example 4 |
| PVA | −4.0 | 63 | Example 3 |
| PEOz | −2.7 | 82 | Example 3 |
| PEG | −1.2 | 84 | Example 3 |
| HPMC | −0.89 | 68 | Example 3 |
| PVP | +1.1 | 70 | Example 3 |
| PAA | +11 | 11 | Comparative Example 4 |
| PLL | +14 | 1.4 | Comparative Example 4 |

Example 4 Elution of a Nucleic Acid Adsorbed on a Gamma Aluminum Oxide Support with a Water-Soluble Neutral Polymer Adsorbed on the Surface Thereof According to Example 1, gamma aluminum oxide with polyethylene glycol adsorbed on the surface thereof was produced, and 0.5 mg of the gamma aluminum oxide was measured out and taken into 1.5-ml tubes. For the eluents, a 0.5M citrate buffer solution (pH5, 6), a 0.5M phosphate buffer solution (pH6, 7, 8), a 0.5M Tris-EDTA buffer solution (pH8), and a 0.5M Tris buffer solution (pH8) to which PVSA was added such that the final concentration would be 10 wt % were used for each tube. Other conditions and procedures were carried out the same way as in Comparative Example 1, and the nucleic acid adsorption ratio, elution ratio, and collection ratio were calculated. Results are shown in Table 4.

These results showed the use of any buffer solution as the eluent could collect the nucleic acid with a high yield.

TABLE 4

| Eluent | Adsorption Ratio [%] | Elution Ratio [%] | Collection Ratio [%] |
|---|---|---|---|
| Citrate Buffer Solution (0.5M, pH5) | 99 | 97 | 96 |
| Citrate Buffer Solution (0.5M, pH6) | 99 | 99 | 98 |
| Phosphate Buffer Solution (0.5M, pH6) | 98 | 98 | 96 |
| Phosphate Buffer Solution (0.5M, pH7) | 97 | 99 | 96 |
| Phosphate Buffer Solution (0.5M, pH8) | 97 | 100 | 97 |
| Tris-EDTA Buffer Solution (0.5M, pH8) | 98 | 86 | 84 |
| PVSA-added Tris Buffer Solution (0.5M, pH8) | 96 | 83 | 80 |

Example 5 Relation Between the Nucleic Acid Collection Ratio Using Gamma Aluminum Oxide with a Water-Soluble Neutral Polymer Adsorbed on the Surface Thereof as a Support and the Nucleic Acid Length According to Example 1, gamma aluminum oxide with polyethylene glycol adsorbed on the surface thereof was produced, and 0.5 mg of the gamma aluminum oxide was measured out and taken into 1.5-ml tubes. As solutions containing a nucleic acid, 100 µl of a 6M aqueous solution of a guanidine thiocyanate salt in which 7.5 µg of a 200 bp fragment, a 300 bp fragment, or a 1000 bp fragment from a 100 bp DNA ladder were individually dissolved was used. Other conditions and procedures were carried out the same way as in Comparative Example 3 to calculate the nucleic acid collection ratio. Results are shown in Table 5.

These results showed that the use of gamma aluminum oxide with a water-soluble neutral polymer, i.e., polyethylene glycol adsorbed on the surface thereof allowed for the efficient collection of the nucleic acid having any length.

TABLE 5

| Base Length | Collection Ratio [%] |
| --- | --- |
| 200 | 60 |
| 300 | 42 |
| 1000 | 51 |

Example 6 Collection of Nucleic Acids from Fetal Bovine Serum

According to Example 1, gamma aluminum oxide with polyethylene glycol adsorbed on the surface thereof was produced, and 1.5 mg of the gamma aluminum oxide was measured out and taken into 1.5-ml tubes. A mixture solution of 100 µl of a 6M aqueous solution of a guanidine thiocyanate salt in which 100 pmol of DNA22 was dissolved as a solution containing a nucleic acid and 100 µl of fetal bovine serum having a protein concentration of 30 mg/ml was used. Other conditions and procedures were carried out the same way as in Comparative Example 3, and the nucleic acid adsorption ratio, elution ratio, and collection ratio were calculated. The same experiment was performed for RNA22 as well. Results are shown in Table 6. The protein concentration in the collection liquid was not more than the detection limit of the Bradford test (0.25 mg/ml or less).

These results showed that the use of the aluminum oxide with polyethylene glycol adsorbed on the surface thereof as a support allowed for the efficient collection of both DNA22 and RNA22 from serum as well.

TABLE 6

| Nucleic Acid | Collection Ratio [%] |
| --- | --- |
| DNA22 | 63 |
| RNA22 | 63 |

Example 7 Effect of the Particle Size of Aluminum Oxide on the Collection of a Nucleic Acid A sieve according to JIS Z-8801-1:2006 defined by Japanese Industrial Standards was used to fractionate gamma aluminum oxide according to the particle size (100 µm or more and less than 212 µm, 40 µm or more and less than 100 µm, 32 µm or more and less than 40 µm, 20 µm or more and less than 32 µm). For the support, as in Example 1, gamma aluminum oxide with polyethylene glycol adsorbed on the surface thereof was prepared for each particle size and used. Other conditions and procedures were carried out the same way as in Comparative Example 3 to calculate the nucleic acid collection ratio. Results are shown in Table 7.

These results showed that any fraction having a particle size of less than 212 µm could collect the nucleic acid.

TABLE 7

| Particle Size [µm] | Adsorption Ratio [%] | Elution Ratio [%] | Collection Ratio [%] |
| --- | --- | --- | --- |
| 100-212 | 70 | 74 | 52 |
| 40-100 | 87 | 88 | 76 |
| 32-40 | 97 | 77 | 74 |
| 20-32 | 99 | 76 | 75 |

Example 8 Difference in the Properties of Gamma Aluminum Oxide in the Collection of a Nucleic Acid Acidic gamma aluminum oxide, neutral gamma aluminum oxide, and basic gamma aluminum oxide were used. For the support, as in Example 1, each gamma aluminum oxide with polyethylene glycol adsorbed on the surface thereof was prepared and used. Other conditions and procedures were carried out the same way as in Comparative Example 3, and the nucleic acid adsorption ratio, elution ratio, and collection ratio were calculated. Results are shown in Table 8.

These results showed that either acidic alumina, neutral alumina or basic alumina could collect the nucleic acid with a high yield.

TABLE 8

| Alumina Property | Adsorption Ratio [%] | Elution Ratio [%] | Collection Ratio [%] |
| --- | --- | --- | --- |
| Acidic | 76 | 75 | 57 |
| Basic | 98 | 86 | 84 |
| Neutral | 90 | 66 | 60 |

Example 9 Effect of the Molecular Weight of a Polymer Adsorbed on the Surface of the Aluminum Oxide Polyethylene glycol having a molecular weight of 6 kD, 10 kD, and 500 kD and polyvinyl alcohol having a molecular weight of 18 kD, 40 kD, and 150 kD (11% acetylation for each) were prepared in a concentration of 10 wt % for each and used polymer solutions. For the support, as in Example 1, gamma aluminum oxide on which polyethylene glycol of each molecular weight was adsorbed on the surface was prepared and used. Other conditions and procedures were carried out the same way as in Comparative Example 3, and the nucleic acid adsorption ratio, elution ratio, and collection ratio were calculated. Results are shown in Table 9.

These results showed that the nucleic acid could be collected with polymers having any molecular weight.

TABLE 9

| Attached Polymer | Molecular Weight [kD] | Adsorption Ratio [%] | Elution Ratio [%] | Collection Ratio [%] |
|---|---|---|---|---|
| PEG | 6 | 98 | 62 | 61 |
| PEG | 10 | 98 | 86 | 84 |
| PEG | 500 | 94 | 49 | 46 |
| PVA | 18 | 92 | 59 | 54 |
| PVA | 40 | 88 | 67 | 59 |
| PVA | 150 | 94 | 47 | 45 |

Example 10 Relation Between the Concentration of the Water-Soluble Neutral Polymer in the Preparation Method of the Support and the Stirring Time Aluminum oxide was measured out in an amount of 0.5 mg, and added to 1.5-ml tubes. As an aqueous polymer solution, 50 μl of polyethylene glycol (PEG, 10 kD), which is a water-soluble neutral polymer, was added to each tube in a concentration of 0.1 wt %, 1 wt %, and 10 wt %, respectively. For each concentration, the resulting mixture was stirred in a mixer for 1 minute, 5 minutes, and 30 minutes. The mixtures were centrifuged by a centrifuge (10000 G, 1 min), and the supernatant was removed. Supports in which polyethylene glycol was adsorbed on the surface of aluminum oxide were thus obtained. As in Comparative Example 3, the nucleic acid collection ratio was further calculated. Results are shown in Table 10.

These results showed that supports produced under any condition could collect the nucleic acid efficiently.

TABLE 10

| Mixing Time | PEG Concentration | Collection Ratio [%] |
|---|---|---|
| 1 min | 0.1 wt % | 51 |
|  | 1 wt % | 55 |
|  | 10 wt % | 95 |
| 5 min | 0.1 wt % | 67 |
|  | 1 wt % | 76 |
|  | 10 wt % | 88 |
| 30 min | 0.1 wt % | 70 |
|  | 1 wt % | 84 |
|  | 10 wt % | 90 |

Example 11 Relation Between the Concentration of the Water-Soluble Neutral Polymer in the Preparation Method of the Support and the Dipping Time Aluminum oxide was measured out in an amount of 0.5 mg, and added to 1.5-ml tubes. As an aqueous polymer solution, 50 μl of polyethylene glycol (PEG, 10 kD), which is a water-soluble neutral polymer, was added to each tube in a concentration of 0.1 wt %, 1 wt %, and 10 wt %, respectively, and left still for 5 minutes and 30 minutes for each. The resulting mixtures were centrifuged by a centrifuge (10000 G, 1 min), and the supernatant was removed. Supports in which polyethylene glycol was adsorbed on the surface of aluminum oxide were thus obtained. As in Comparative Example 3, the nucleic acid collection ratio was further calculated. Results are shown in Table 11.

These results showed that supports produced under any condition could collect the nucleic acid efficiently.

TABLE 11

| Mixing Time | PEG Concentration | Collection Ratio [%] |
|---|---|---|
| 5 min | 0.1 wt % | 29 |
|  | 1 wt % | 31 |
|  | 10 wt % | 61 |
| 30 min | 0.1 wt % | 48 |
|  | 1 wt % | 53 |
|  | 10 wt % | 75 |

Example 12 Relation Between the Presence or Absence of a Centrifugation in the Production Method of the Support and the Nucleic Acid Collection Ratio Aluminum oxide was measured out in an amount of 0.5 mg, and added to a 1.5-ml tube. As an aqueous polymer solution, 50 μl of polyethylene glycol (PEG, 10 kD), which is a water-soluble neutral polymer, was added to the tube in a concentration of 10 wt % and stirred for 10 minutes in a mixer. After this, while a centrifugation by a centrifuge and a procedure to remove the supernatant were carried out in Example 2, these procedures were omitted in Example 12. Except that the support was produced this way, this Example was carried out the same way as in Comparative Example 3, and the nucleic acid adsorption ratio, elution ratio, and collection ratio were calculated and results were shown in Table 12.

Among the results from Example 2 in which the nucleic acid was collected using the supports produced in Example 1, in comparison with the results of the nucleic acid collection ratio in which polyethylene glycol was used as the water-soluble neutral polymer, these results showed that either method of producing the support could collect the nucleic acid efficiently.

TABLE 12

| Centrifugation | Adsorption Ratio [%] | Elution Ratio [%] | Collection Ratio [%] | |
|---|---|---|---|---|
| With | 98 | 86 | 84 | Example 2 |
| Without | 98 | 91 | 89 | Example 12 |

Example 13 Relation Between the Removal by Water Washing of the Water-Soluble Neutral Polymer in the Production Method of the Support and the Collection Ratio According to Example 1, aluminum oxide with polyethylene glycol adsorbed on the surface thereof was produced. Then, 200 μl of water was added to this support, and the mixture was stirred in a mixer for 1 minute, and centrifuged by a centrifuge (10000 G, 1 min), and the supernatant was removed. Two supports were prepared by carrying out this washing procedure once for one support and three times for the other. Except that the support was produced this way, this Example was carried out the same way as in Comparative Example 3, and the nucleic acid adsorption ratio, elution ratio, and collection ratio were calculated, and results were shown in Table 13.

Among the results from Example 2 in which the nucleic acid was collected using the supports produced in Example 1, in comparison with the results of the nucleic acid collection ratio in which polyethylene glycol was used as the water-soluble neutral polymer, these results showed that either method of producing the support could collect the nucleic acid efficiently.

TABLE 13

| Number of Water Washing | Adsorption Ratio [%] | Elution Ratio [%] | Collection Ratio [%] | |
|---|---|---|---|---|
| None | 98 | 86 | 84 | Example 2 |
| Once | 91 | 48 | 43 | Example 13 |
| Three Times | 91 | 30 | 27 | Example 13 |

Example 14 Relation Between the Surface Coverage Ratio of the Aluminum Oxide by the Polymer in the Support and the Collection Ratio The support produced in Example 13, the aluminum oxide produced in Example 2 with polyethylene glycol adsorbed on the surface thereof (no water washing), aluminum oxide on which polymer was not adsorbed, and polyethylene glycol were analyzed by a surface potential microscope. A potential map was thus obtained and the average potential was calculated. For the measurement, a support sample was dispersed on a carbon tape and was measured in the air at room temperature within the view range of 0.5 μm×1 μm on a non-contact mode, using a CoCr-coated silicon cantilever. For measured values, three particles were randomly selected from the support with polyethylene glycol adsorbed on the surface thereof, and the average value of estimated values was used. With the coverage ratio of the aluminum oxide alone without an adsorbed polymer as 0% and that of the polyethylene glycol alone as 100%, the ratio of the average potential of the aluminum oxide with polyethylene glycol adsorbed to that of polyethylene glycol was obtained to calculate the surface coverage ratio. The relation between the surface coverage ratio and the nucleic acid collection ratio when each support was used was shown in Table 14.

These results showed the use of the support with the surface coverage ratio of 7% or more could collect the nucleic acid efficiently.

TABLE 14

| Support | Surface Coverage [%] | Collection Ratio [%] | |
|---|---|---|---|
| Water Washing: None | 100 | 84 | Example 2 |
| Water Washing: Once | 40 | 43 | Example 13 |
| Water Washing: Three Times | 7 | 27 | Example 13 |

INDUSTRIAL APPLICABILITY

We provide efficient collection of a nucleic acid(s) from a very short nucleic acid(s) such as pre-miRNA or miRNA to a long nucleic acid(s) of 1000 bases or more from a biological sample in an easy method without using any organic solvent.

The invention claimed is:

1. A method of collecting a nucleic acid(s) from a biological sample, comprising:
   step a) adsorbing a water-soluble neutral polymer on a surface of an aluminum oxide support, followed by applying a solution containing the nucleic acid(s) to the surface of the aluminum oxide support to thereby adsorb the nucleic acid(s) to the aluminum oxide support,
   step b) separating the aluminum oxide support on which the nucleic acid(s) is/are adsorbed from the solution, and
   step c) collecting the nucleic acid(s) by adding an eluent to the aluminum oxide support on which the nucleic acid(s) is/are adsorbed and which is separated in step b), wherein the polymer is selected from the group consisting of polyethylene glycol, polyvinyl alcohol, polyvinylpyrrolidone, poly(2-ethyl-2-oxazoline) and hydroxylpropyl methylcellulose,
   the polymer has a molecular weight of 5 kD to 500 kD, and
   the concentration of the polymer in step a) is 0.1 wt % or more,
   wherein the water-soluble neutral polymer is not covalently bound to the aluminum oxide support.

2. The method according to claim 1, wherein the water-soluble neutral polymer is a polymer having a zeta potential of not less than −10 mV and not more than +10 mV in a solution of pH 7.

3. The method according to claim 1, wherein the eluent is a buffer solution.

4. The method according to claim 1, wherein the biological sample is blood, urine, saliva, a mucous membrane, sweat, a cultured cell, a culture solution of cultured cells, or a tissue sample or specimen.

5. The method according to claim 2, wherein the eluent is a buffer solution.

6. The method according to claim 2, wherein the biological sample is blood, urine, saliva, a mucous membrane, sweat, a cultured cell, a culture solution of cultured cells, or a tissue sample or specimen.

7. The method according to claim 3, wherein the biological sample is blood, urine, saliva, a mucous membrane, sweat, a cultured cell, a culture solution of cultured cells, or a tissue sample or specimen.

8. The method according to claim 1, wherein the support in step a) is produced by bringing the polymer solution into contact with the aluminum oxide.

* * * * *